United States Patent [19]

Kida et al.

[11] 4,362,663

[45] Dec. 7, 1982

[54] MAYTANSINOID COMPOUND

[75] Inventors: Makoto Kida, Kawanishi; Motowo Izawa, Amagasaki; Kazuo Nakahama, Muko, all of Japan

[73] Assignee: Takeda Chemical Industries, Ltd., Osaka, Japan

[21] Appl. No.: 188,239

[22] Filed: Sep. 17, 1980

[30] Foreign Application Priority Data

Sep. 21, 1979 [JP] Japan ................................ 54-122217

[51] Int. Cl.$^3$ .......................................... C07D 498/18
[52] U.S. Cl. .............................. 260/239.3 P; 435/119; 435/872; 424/248.54
[58] Field of Search ................... 260/239.3 P, 239.3 T

[56] References Cited

U.S. PATENT DOCUMENTS 4,162,940 7/1979 Higashide et al. ........... 260/239.3 P
4,322,348 3/1982 Asai et al. ...................... 260/239.3 P

*Primary Examiner*—Robert T. Bond
*Attorney, Agent, or Firm*—Wegner & Bretschneider

[57] ABSTRACT

Antibiotic C-15003 PND of the formula:

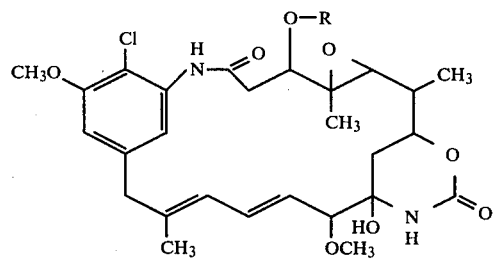

wherein R is H or alkanoyl containing not more than 5 carbon atoms is produced by contacting a maytansinoid compound with a culture broth, inclusive of a processed matter derived therefrom, of a microorganism belonging to one of the genera Streptomyces and Chainia which is able to transform said maytansinoid compound into Antibiotic C-15003 PND.

Antibiotic C-15003 PND is useful as antitumor, antifungal or antiprotozoal agent.

1 Claim, No Drawings

MAYTANSINOID COMPOUND

This invention relates to a method of producing Antibiotic C-15003 PND.

Several Antibiotic C-15003 PND compounds can be obtained by cultivating a microorganism, for example *Nocardia* sp. No. C-15003 [deposited at Fermentation Research Institute, Agency of Industrial Science and Technology, Japan under the number of FERM-P No. 3992, Institute for Fermentation, Osaka, Japan under the accession number of IFO 13726 and The American Type Culture Collection, U.S.A., under the number of ATCC 31281], in a culture medium and harvesting and purifying them from the fermentation broth. These substances have potent antitumor activity.

The present inventors explored microbiological methods for a transformation of maytansinoid compounds [e.g. the compounds described in Nature, London, 270, 721 (1977) and Tetrahedron 35, 1079 (1979)] into other compounds, and discovered that when a culture broth, inclusive of processed matters derived therefrom, of one of certain microorganisms is permitted to act upon maytansinoid compounds, the latter are converted to Antibiotic C-15003 PND and that when the resulting compounds are deacylated, the corresponding compounds having a hydroxyl group in 3-position are obtained. The above finding was followed by further research which has resulted in the present invention.

This invention, therefore, relates to:
(1) a method of producing Antibiotic C-15003 PND (I) of the formula (I):

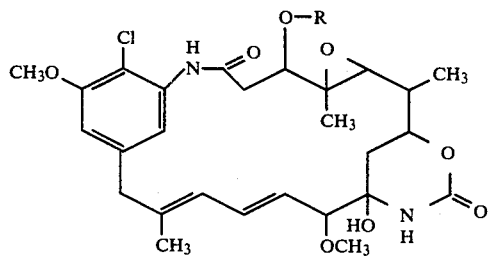

wherein R is H or alkanoyl containing not more than 5 carbon atoms
characterized by contacting a maytansinoid compound of the formula (II)

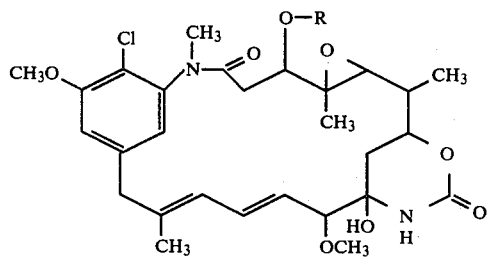

wherein R is as defined above
with a culture broth, inclusive of a processed matter derived therefrom, of a microorganism belonging to one of the genera Streptomyces and Chainia which is able to transform said maytansinoid compound (II) into Antibiotic C-15003 PND (I), and, if required, thus obtained compound of the formula (III)

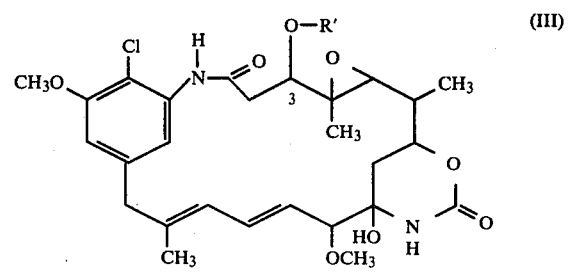

wherein R' is alkanoyl containing not more than 5 carbon atoms is subjected to deacylation;
and (2) C-15003 PND-0 of the general formula (IV)

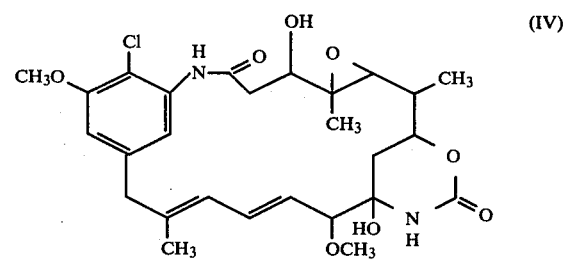

Referring to the above general formulas, the alkanoyl of not more than 5 carbon atoms as designated by R or R' may for example be formyl (—CHO), acetyl (—COCH₃), propionyl (—COCH₂CH₃), butyryl (—COCH₂CH₂CH₃), isobutyryl

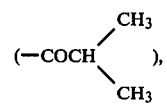

valeryl (—COCH₂CH₂CH₂CH₃), isovaleryl (—COCH₂

or the like.

The term "C-15003 PND" or, simply, "PND" as used throughout this specification means all of the compounds of general formula (I), a mixture of two or more of such compounds or any one of the compounds. The compound of formula (I) wherein R is hydrogen, i.e. the compound of formula (IV), will hereinafter be referred to as "C-15003 PND-0" or briefly as "PND-0"; the compound of formula (I) wherein R is —COCH₃ will be referred to as "C-15003 PND-1" or briefly as "PND-1"; the compound (I) wherein R is —COCH₂CH₃ will be referred to as "C-15003 PND-2" or briefly as "PND-2"; the compound (I) wherein R is

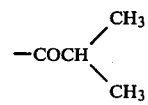

will be referred to as "C-15003 PND-3" or briefly as "PND-3"; and the compound (I) wherein R is

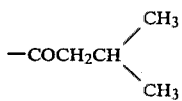

will be referred to as "C-15003 PND-4" or briefly as "PND-4".

The compound of general formula (II) wherein R is H, i.e. maytansinol, will hereinafter be referred to "P-0"; the compound (II) wherein R is —COCH$_3$, i.e. maytanacine, will be referred to as "P-1"; the compound (II) wherein R is —COCH$_2$CH$_3$, i.e. maytansinol propionate, will be referred to as "P-2"; the compound (II) wherein R is

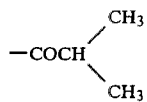

will be referred to as "C-15003 P-3" or briefly as "P-3"; the compound (II) wherein R is —COCH$_2$CH$_2$CH$_3$ will be referred to as "C-15003 P-3'" or briefly as "P-3'"; and the compound (II) wherein R is

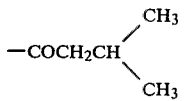

will be referred to as "C-15003 P-4" or briefly as "P-4".

The term "C-15003" means all of the compounds of P-0, P-1, P-2, P-3, P-3' and P-4, a mixture of two or more of the compounds or any one of the compounds.

P-0, P-1, P-2, P-3, P-3' and P-4 can be obtained by cultivating a microorganism, for example *Nocardia* sp. No. C-15003 [FERM-P No. 3992; IFO 13726; ATCC-31281], in a culture medium and harvesting and purifying them from the fermentation broth [Nature vol. 270, p. 721 (1977), Tetrahedron 35 1079 (1979), U.S. Pat. No. 4,151,042, U.S. Pat. No. 4,162,940.].

The strain ATCC 31281 is listed on "The American Type Culture Collection Catalogue of Strains I (Fourteenth Edition 1980)".

P-0 can also be obtained by deacylating P-3, P-3' and/or P-4 [Nature, vol. 270, p. 271 (1977), Tetrahedron 35, 1079, U.S. Pat. No. 4,162,940.].

The compounds of general formula (II) wherein R is a substituent other than a hydrogen atom can be produced by reacting P-0 with an acid anhydride of general formula:

 (V)

[wherein R' is as defined above]
derived from the corresponding carboxylic acid or with an acid halide of general formula:

R'X (VI)

[wherein R' is as defined above; X is halogen]

which is also derived from the corresponding carboxylic acid.

Referring to the above general formula (VI), the halogen X may for example be chlorine, bromine or iodine. There are cases in which the above reaction is preferably carried out in the presence of a base. As examples of the base may be mentioned tertiary amines such as triethylamine, tributylamine, pyridine, 4-dimethylaminopyridine, α-, β- or γ-picoline, 2,6-lutidine, dimethylaniline, diethylaniline, N-methylmorpholine, etc. Also, the above reaction may be conducted in an appropriate solvent which may for example be esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, dimethylformamide, dimethyl sulfoxide, sulfolane, etc. as well as mixtures of such solvents. It is also possible to employ the above-mentioned base as the solvent, or a mixture of the base with the solvent mentioned above. While the reaction temperature is not particularly critical, the reaction is desirably carried out at $-20°$ C. to $+40°$ C. The resulting compound of general formula (II) wherein R is a substituent group other than H can be purified by routine separation and purification procedures such as solvent extraction, chromatography, recrystallization, etc.

The microorganism employed in the method of this invention may be any organism belonging to one of the genera Streptomyces and Chainia which is capable of transforming the maytansinoid compound (II) into C-15003 PND (I), inclusive of variants and mutants thereof. Thus, as examples of organisms which can be employed in the practice of this invention there may be mentioned *Streptomyces minutiscleroticus* IFO 13361 (ATCC 17757, 19346), *Streptomyces roseiscleroticus* IFO 13363 (ATCC 17755), *Streptomyces flaviscleroticus* IFO 13357 (ATCC 19347), *Streptomyces olivaceiscleroticus* IFO 13484 (ATCC 15722), *Streptomyces sclerotialus* IFO 12246 (ATCC 15721) and *Chainia nigra* IFO 13362 (ATCC 17756).

The above-mentioned strains are listed on "Institute for Fermentation Osaka List of Cultures (1978 sixth edition)", and the strains referred with ATCC numbers are listed on "The American Type Culture Collection Catalogue of Strains I (Thirteenth Edition 1978)".

Generally, organisms of the genera Stereptomyces and Chainia are highly variable in characteristics and can be mutated by artificial means such as X-ray, UV, gamma-ray or other irradiation, or with a mutagenic agent (e.g. nitrosoguanidine, ethyleneimine, etc.). Even such mutants can also be employed for the purposes of this invention only if they are still able to transform the maytansinoid compound (II) into C-15003 PND (I).

The medium used for the cultivation of said microorganism in the method according to this invention may be a liquid medium or a solid medium, if it contains sources of nutrients which said microorganism can utilize, although a liquid medium is preferred for high production runs. In the medium are incorporated the carbon sources which said organism can assimilate, the nitrogen sources which it can digest, inorganic substances, trace nutrients and so forth in suitable proportions. The carbon sources may include, among others, glucose, lactose, sucrose, maltose, dextrin, starch, glycerol, mannitol, sorbitol, etc., oils and fats (e.g. soybean oil, lard oil, chicken oil, etc.), etc. The nitrogen sources may include, among others, meat extract, yeast extract, dried yeast, soybean flour, corn steep liquor, peptone, cotton-seed flour, spent molasses, urea, ammonium salts (e.g. ammonium sulfate, ammonium chloride, ammonium nitrate, ammonium acetate, etc.) and the like. In addition, use may also be made of salts of sodium, potassium, calcium, magnesium, etc., metal salts such as salts of iron, manganese, zinc, cobalt, nickel, etc.; salts of phosphoric acid, boric acid, etc; and salts of organic acids, such as salts of acetic acid, propionic acid, etc. It is further possible to incorporate amino acids (e.g. glutamic acid, aspartic acid, alanine, glycine, lysine, methionine, proline, etc.), peptides (e.g. dipeptides, tripeptides, etc.), vitamins (e.g. $B_1$, $B_2$, nicotinic acid, $B_{12}$, C, E, etc.), nucleic acids (e.g. purine, pyrimidine and their derivatives) and so forth. Of course, it is possible to add inorganic or organic acids, alkalis, buffers, etc. for the purpose of adjusting the pH of medium or to add a suitable amount of oils, surfactants, etc. for defoaming purposes.

The cultivation method may be stationary culture, shake culture or aerated stirring culture. For high production runs, the so-called submerged aerobic culture is of course desirable. While cultivation conditions depend upon the condition and composition of medium, the particular strain of organism, cultural method employed and so forth, generally the cultivation is desirably carried out at a temperature in the range of 20° C. to 45° C. and at an initial pH level of near neutral. It is especially desirable to maintain the temperature at 24° C. to 37° C. at an intermediate phase of cultivation and start the cultivation at pH 6.5 to 8.5. The cultivation time may range from 6 to 100 hours and the range of 16 to 48 hours is particularly desirable.

The term 'culture broth' as used in this specification means the broth obtained by the above-described cultivation procedure.

The term 'processed matter' means the mycelial or cellular products obtained from said culture broth by a physical or/and chemical treatments, e.g. filtration, centrifugation, super-sonication, French-press process, grinding with alumina, treatment with bacteriolytic enzymes, treatment with a surfactant or organic solvent, etc., or an equivalent milled product containing a demethylating enzyme. It is also possible to employ the corresponding demethylating enzyme obtained by a conventional purification procedure or such demethylating enzyme as immobilized by a conventional procedure.

The method of this invention is carried into practice by contacting the starting compound (II) with the culture broth or processed matter as obtained or derived from the above-mentioned microorganism. The concentration of said starting compound in the reaction system is preferably in the range of 100 to 500 μg/ml. The reaction temperature and pH are desirably 20° to 50° C. and pH 5 to 10, and more desirably about 24° to 40° C. and pH 6 to 9. The reaction time is 1 to 100 hours and, more desirably 24 to 72 hours. The reaction may be conducted under stationary, shake, aerated or stirring conditions, although shake, aerated or stirring conditions are preferred.

The PND obtainable in the above manner can be detected by thin-layer chromatography (TLC hereinafter). Thus, the reaction mixture is extracted with ethyl acetate, concentrated to 1/100 by volume and subjected to TLC on a silica gel glass plate (Merck, Germany, Kieselgel 60$F_{254}$, 0.25 mm, 20×20 cm) with $H_2O$-saturated ethyl acetate, detection being made with ultraviolet light at 2537 Å.

Since the product substance group is neutral lipophilic properties, the desired compound can be isolated from the reaction system by means of the isolation and purification procedures normally applied to the recovery of microbial metabolites. Such procedures are exemplified by procedures utilizing differences in solubility with respect to impurities, procedures utilizing differences in adsorptive affinity for various adsorbents such as activated carbon, macroporous nonionic resin, silica gel, alumina, etc., and procedures for removing impurities with ion exchange resins, and these procedures may be used either independently, in combination or in repetition. The suitable solvent for use in procedures utilizing a solubility difference include, for example, water-immiscible organic solvents such as fatty acid esters (e.g. ethyl acetate, amyl acetate, etc.), alcohols (e.g. butanol, etc.), halogenated hydrocarbons (e.g. chloroform, etc.), and ketones (e.g., methyl isobutyl ketone, etc.). The extraction is carried out near neutral pH and a preferred procedure comprises adjusting the broth filtrate to pH 7 and extracting it with ethyl acetate. The extract is then washed with water and concentrated under reduced pressure, and a nonpolar solvent such as petroleum ether or hexane is added. The crude product (i) containing the activity is thus obtained. Since the TLC of this crude product gives many spots other than the desired product compound PND, the following stepwise purification process is applied. Thus, as routine methods, various adsorption chromatographic techniques can be successfully utilized. While the adsorbents may be those commonly employed, e.g. silica gel, alumina, macroporous nonionic adsorbent resin, etc., silica gel is most effective for purification from crude product (i). The adsorbent column is developed first with, for example, a nonpolar solvent such as petroleum ether or/and hexane and, then, with the addition of a polar solvent or solvent system such as ethyl acetate, acetone, ethanol or/and methanol, whereby the desired compound PND is eluted. As an example, column chromatography on silica gel (0.05–0.2 mm) is carried out and the chromatogram is developed with sequential increases in the ratio of ethyl acetate to hexane. The eluate is scanned by TLC and the fractions containing PND are combined, concentrated under reduced pressure and treated with petroleum ether or hexane to recover a crude product (ii). Since this product still contains much impurities, it is further purified. By way of example, such further purification can be achieved on a second silica gel column using a different solvent system. As to the developing solvents, the column is developed first with a halogenated hydrocarbon such as dichloromethane, chloroform, etc. and then with addition of a polar solvent or solvent system such as alcohol (e.g. ethanol, methanol, etc.) or/and ketone (e.g. acetone, methyl ethyl ketone, etc.), whereby the desired compound PND is isolated. The solvents for said first and second silica gel columns may be reversed or identical. It is also possible to use other common organic solvents in various combinations.

When a macroporous adsorbent resin is used for the purification of crude product (ii), PND is eluted with a mixture of water with a lower alcohol, lower ketone or ester. The lower alcohol is exemplified by methanol, ethanol, propanol, butanol, etc., the lower ketone by acetone, methyl ethyl ketone, etc., and the ester by ethyl acetate, etc. For example, the crude product (ii) is dissolved in 50 V/V % aqueous methanol, the solution is passed through a column of Diaion HP-10 (Mitsubishi Chemical Industries, Ltd., Japan,) the column is washed with 60 V/V % aqueous methanol, and the desired product PND is eluted with 90 V/V % aqueous methanol.

Then, for the isolation of PND-0, PND-1 PND-2 and PND-3, for instance, the fractions are concentrated under reduced pressure and crystallized from ethyl acetate.

As to PND-4, the fraction is concentrated under reduced pressure and treated with petroleum ether to obtain powdery product.

PND can be used also as intermediate materials for the synthesis of pharmaceutically useful compounds. Thus, by deacylating a PND [the compound (III)] other than PND-0, there can be obtained the novel compound PND-0 having a hydroxyl group in 3-position. In this case, because the acyl group is in the position beta to the carbonyl group, the conventional reductive hydrolysis reaction can be employed with advantage. Thus, by using a metal hydride complex compound [e.g. lithium aluminum hydride (LiAlH$_4$)] at a low temperature (e.g. $-20°$ to $0°$ C.), the O-ester bond in 3-position can be hydrolyzed without affecting under functional groups, e.g. the carbonyl, epoxy, carbon-carbon double bond, etc., so as to yield a compound PND-0. The isolation and purification of PND-0 can be performed in the same manner as described hereinbefore.

Referring to the deacylation reaction, PND [compound iii)] other than PND-0 can be transformed into PND-0 by contacting the former with a culture broth, inclusive of any processed matter derived therefrom, of a Streptomyces strain.

The microorganism to be employed in the practice of this invention may be an organism, inclusive of mutants thereof, which belongs to the genus Streptomyces and which is able to transform the 3-acyloxy group of compound (III) into a hydroxyl group. As an example of the microorganism which can be employed in the practice of this invention, there may be mentioned *Streptomyces coelicolor* ATCC 13405 (IFO-3807). The above ATCC 13405 strain is listed on The American Type Culture Collection Catalogue of Strains I (Thirteenth Edition 1978) and is available from ATCC. The strain can also be obtained from Institute for Fermentation, Osaka as the IFO 3807 strain.

Generally, organisms of the genera Streptomyces are highly variable in characteristics and can be mutated by artificial means such as X-ray, UV, or other irradiation, or with a mutagenic agent (e.g. nitrosoguanidine, ethyleneimine, etc.). Even such mutants can also be employed for the purposes of this invention only if they are still able to transform the 3-acyloxy group of compound (III) into a hydroxyl group.

The medium used for the cultivation of said microorganism in the method according to this invention may be a liquid medium or a solid medium, if it contains sources of nutrients which said microorganism can utilize, although a liquid medium is preferred for high production runs. In the medium are incorporated the carbon sources which said organism can assimilate, the nitrogen sources which it can digest, inorganic substances, trace nutrients and so forth in suitable proportions. The carbon sources may include, among others, glucose, lactose, sucrose, maltose, dextrin, starch, glycerol, mannitol, sorbitol, etc., oils and fats (e.g. soybean oil, lard oil, chicken oil, etc.), etc. The nitrogen sources may include, among others, meat extract, yeast extract, dried yeast, soybean flour, corn steep liquor, peptone, cotton-seed flour, spent molases, urea, ammonium salts (e.g. ammonium sulfate, ammonium chloride, ammonium nitrate, ammonium acetate, etc.) and the like. In addition, use may also be made of salts of sodium, potassium, calcium, magnesium, etc., metal salts such as salts of iron, manganese, zinc, cobalt, nickel, etc.; salts of phosphoric acid, boric acid, etc., and salts of organic acids such as salts of acetic acid, propionic acid, etc. It is further possible to incorporate amino acids (e.g. glutamic acid, aspartic acid, alanine, glycine, lysine, methionine, proline, etc.), peptides (e.g. dipeptides, tripeptides, etc.), vitamins (e.g. $B_1$, $B_2$, nicotinic acid, $B_{12}$, C, E, etc.), nucleic acids (e.g. purine, pyrimidine, and their derivatives) and so forth. Of course, it is possible to add inorganic or organic acids, alkalis, buffers, etc. for the purpose of adjusting the pH of medium or to add a suitable amount of oils, surfactants, etc. for defoaming purposes.

The cultivation method may be stationary culture, shake culture or aerated stirring culture. For high production runs, the so-called submerged aerobic culture is of course desirable. While cultivation conditions depend upon the condition and composition of medium, the particular strain of organism, cultural method employed and so forth, generally the cultivation is desirably carried out at a temperature in the range of 20° C. to 45° C. and at an initial pH level of near neutral. It is especially desirable to maintain the temperature at 24° C. to 37° C. at an intermediate phase of cultivation and start the cultivation at a pH of 6.5 to 8.5. The cultivation time may range from 6 to 100 hours and the range of 16 to 60 hours is particularly desirable.

The term 'culture broth' as used in this specification means are broth obtained by the above-described cultivation procedure.

The term 'processed matter' means the mycelial or cellular products obtained from said culture broth by a physical or/and chemical treatments, e.g. filtration, centrifugal separation, sonication, French-press process, grinding with alumina, treatment with bacteriolytic enzymes, treatment with a surfactant or organic solvent, etc., or an equivalent milled product containing a deacylating enzyme. It is also possible to employ the corresponding deacylating enzyme obtained by a conventional purification procedure or the cells or deacylating enzyme as immobilized by a conventional procedure.

The method of this invention is carried into practice by contacting the starting compound (II) with the culture broth or processed matter as obtained or derived from the above-mentioned microorganism. The concentration of said starting compound in the reaction system is preferably in the range of 1 to 200 μg/ml. The reaction temperature and pH are desirably 20° to 50° C. and pH 5 to 10, and more desirably about 24° to 40° C. and pH 6 to 9. The reaction time is 10 minutes to 100 hours and, more desirably 1 to 48 hours. The reaction may be conducted under stationary, shake, aerated or stirring conditions, although shake, aerated or stirring conditions are preferred.

The product obtainable in the above manner can be detected by thin-layer chromatography (TLC hereinafter). Thus, the reaction mixture is extracted with ethyl acetate, concentrated to 1/100 by volume and subjected to TLC on a silica gel glass plate (Kieselgel 60F.$_{254}$, 0.25 mm, 20×20 cm) with a solvent system of chloroform and methanol (9:1), detection being made with ultraviolet light at 2537 Å.

To isolate PND-0 from the reaction mixture, the same separation and purification procedures as described hereinbefore can be utilized.

PND-4 as obtained in Example 4, PND-3 as obtained in Example 2, PND-2 as obtained in Example 9 and PND-1 as obtained in Example 7, all the Examples appearing hereinafter, have the physicochemical properties shown in Table 1.

(2) Melting point: 189°–191° C.

(3) Optical rotation: $[\alpha]_D^{22} - 128° \pm 10°$ (C=0.25, chloroform)

(4) Elemental analysis: (Found) C 58.59; H 6.62; N 4.81; Cl 6.27; (calcd.) C 58.85; H 6.40; N 5.08; Cl 6.43

(5) Ultraviolet absorption spectrum: $\lambda_{max}^{MeOH}$ 231 nm ($\epsilon$32500), 239(33000),250(sh 28400), 278(4060),287(3900)

(6) Infrared absorption spectrum: $\nu$KBr 1675, 1590, 1430, 1393, 1304, 1178, 1093, 1063 cm$^{-1}$

TABLE 1

| | C-15003PND-1<br>$C_{29}H_{37}ClN_2O_9$<br>= 593.089 | C-15003PND-2<br>$C_{30}H_{39}ClN_2O_9$<br>= 607.115 | C-15003PND-3<br>$C_{31}H_{41}ClN_2O_9$<br>= 621.141 | C-15003PND-4<br>$C_{32}H_{43}ClN_2O_9$<br>= 635.167 |
|---|---|---|---|---|
| Appearance | White powder | White powder | White powder | White powder |
| Optical rotation $[\alpha]_D^{22}$ (in ethanol) | $-55.8° \pm 10°$ (c = 0.12) | $-56.3° \pm 10°$ (c = 0.14) | $-57.1° \pm 10°$ (c = 0.14) | $-56.6° \pm 10°$ (c = 0.415) |
| Elemental analysis Found (%) | C 58.34<br>H 6.52<br>N 4.66<br>Cl 5.81 | C 59.10<br>H 6.72<br>N 4.77<br>Cl 5.68 | C 59.63<br>H 6.82<br>N 4.67<br>Cl 5.38 | C 60.04<br>H 6.97<br>N 4.37<br>Cl 5.44 |
| Elemental analysis Calcd. (%) | C 58.73<br>H 6.29<br>N 4.72<br>Cl 5.98 | C 59.35<br>H 6.48<br>N 4.61<br>Cl 5.84 | C 59.94<br>H 6.65<br>N 4.51<br>Cl 5.71 | C 60.51<br>H 6.82<br>N 4.41<br>Cl 5.58 |
| Ultraviolet absorption spectrum nm ($\epsilon$) (in methanol) | 232 (31500)<br>239 (32000)<br>252 (sh 28600)<br>279 (3780)<br>288 (3700) | 232 (31000)<br>239 (32000)<br>252 (sh 28200)<br>279 (3800)<br>288 (3760) | 232 (32500)<br>239 (33000)<br>252 (sh 28400)<br>279 (3880)<br>288 (3790) | 232 (sh 31500)<br>239 (31100)<br>252 (sh 27600)<br>279 (3760)<br>288 (3690) |
| | PND-1 | PND-2 | PND-3 | PND-4 |
| Infrared absorption specturm (cm$^{-1}$) (KBr) | 1740, 1730, 1590, 1455, 1425, 1390, 1145, 1100, 1080 | 1740, 1730, 1590, 1455, 1425, 1390, 1145, 1100, 1080 | 1740, 1730, 1590, 1455, 1425, 1390, 1145, 1100, 1080 | 1740, 1730, 1590, 1455, 1425, 1390, 1145, 1100, 1080 |
| Nuclear magnetic resonance spectrum (ppm) 90 MHz, CDCl$_3$ | 1.13(3H,s)<br>1.24(3H,d)<br>1.76(3H,s)<br>3.38(3H,s)<br>3.95(3H,s), etc. | 1.12(3H,s)<br>1.26(3H,d)<br>1.76(3H,s)<br>3.37(3H,s)<br>3.95(3H,s), etc. | 1.10(3H,s)<br>1.20(3H,d)<br>1.75(3H,s)<br>3.35(3H,s)<br>3.95(3H,s), etc. | 1.14(3H,s)<br>1.26(3H,d)<br>1.76(3H,s)<br>3.39(3H,s)<br>3.94(3H,s), etc. |
| Mass spectrum (m/e) | 592, 577, 531, 471, 456, 436 | 606, 591, 545, 471, 456, 436 | 620, 605, 559, 471, 456, 436 | 634, 619, 573, 471, 456, 436 |
| Solubility | Petroleum ether, n-hexane, water: insoluble<br>Chloroform, ethyl acetate, acetone, ethanol, methanol, pyridine, tetrahydrofuran, dimethylsulfoxydo: soluble | Petroleum ether, n-hexane, water: insoluble<br>Chloroform, ethyl acetate, acetone, ethanol, methanol, pyridine, tetrahydrofuran, dimethylsulfoxydo: soluble | Petroleum ether, n-hexane, water: insoluble<br>Chloroform, ethyl acetate, acetone, ethanol, methanol, pyridine, tetrahydrofuran, dimethylsulfoxydo: soluble | Petroleum ether, n-hexane, water: insoluble<br>Chloroform, ethyl acetate, acetone ethanol, methanol, pyridine, tetrahydrofuran, dimethylsulfoxydo: soluble |
| Color reaction | Dragendorff: positive<br>Beilstein: positive | Dragendorff: positive<br>Beilstein: positive | Dragendorff: positive<br>Beilstein: positive | Dragendorff: positive<br>Beilstein: positive |
| Thin-layer chromatography (Rf)<br>(1) Merck silica gel<br>(2) Merck silica gel Reversed phase gel glass plate<br>(3) Merck Rp-18F$_{254}$ | (1) Chloroform-methanol (9:1) 0.45<br>(2) H$_2$O-saturated ethyl acetate 0.37<br>(3) 80% aqueous methanol 0.64 | (1) Chloroform-methanol (9:1) 0.47<br>(2) H$_2$O-saturated ethyl acetate 0.42<br>(3) 80% aqueous methanol 0.61 | (1) Chloroform-methanol (9:1) 0.49<br>(2) H$_2$O-saturated ethyl acetate 0.48<br>(3) 80% aqueous methanol 0.58 | (1) Chloroform-methanol (9:1) 0.51<br>(2) H$_2$O-saturated ethyl acetate 0.55<br>(3) 80% aqueous methanol 0.55 |

The physicochemical properties of PND-0 as obtained in Example 13 which appears hereinafter as dried over phosphorus pentoxide at 40° C. and under reduced pressure for 8 hours are as set forth below.

TABLE 2

PND-0 $C_{27}H_{35}ClN_2O_8 = 551.050$ (1) Appearance: Colorless needles (7) Nuclear magnetic resonance spectrum: (CDCl$_3$, 90 MHz) $\delta$0.98(3H,s),1.27(3H,d),1.67(3H,s),3.33(3H,s),3.92(3H,s), etc.

(8) Mass spectrum: m/e 550, 489, 471, 456, 454

(9) Solubility: Petroleum ether, n-hexane, water: insoluble; Chloroform, ethyl acetate, acetone, ethanol, methanol, pyridine, tetrahydrofuran, dimethylsulfoxydo: soluble

(10) Color reaction: Dragendorff; positive; Beilstein; positive

(11) Thin-layer chromatography: (Rf)
  (1) Chloroform-methanol (9:1): 0.30 (Merck silica gel)
  (2) H₂O-saturated ethyl acetate: 0.25 (Merck silica gel)
  (3) 80% Aqueous methanol: 0.61 (Merck RP-18F₂₅₄)

P-0 (maytansinol) which is obtainable by reductive cleavage-reaction of P-1, P-2, P-3, P-3' and P-4 is identical with maytansinol which is the nucleus of maytansine [Nature 270, 721-722 (1977), Tetrahedron 35, 1079-1085 (1979)], and as mentioned hereinbefore, P-0, P-1 and P-2 repsectively correspond to maytansinol, maytanacine and maytansinol propionate which are described in Journal of the American Chemical Society 97, 5294 (1975). Therefore, the absolute configurations of asymmetric carbon atoms $C_3$, $C_4$, $C_5$, $C_6$, $C_7$, $C_9$ and $C_{10}$ contained in P-0 (maytansinol) are the same as those of maytansine as reported in Journal of the American Chamical Society 94, 1354-1356 (1972). Thus, the absolute configurations of such asymmetric carbon atoms in PND are all the same as the above.

The above-mentioned physicochemical properties, taken together with the antimicrobial and antitumor activities described hereinafter, suggest at once that PND compounds have a structure similar to C-15003. The fact that the mass spectra of PND-0, PND-1, PND-2, PND-3 and PND-4 show m/e 471, 456 and 436 as the common mass numbers indicates that these compounds have the same nucleus but different side-chain ester residues. Moreover, the characteristic fragment peaks $M^+ - a$ (a = NHCO.H₂O) and $M^+ - (a+b)$ (b = R—OH) of maytansinoid compounds are as follows.

|       | $M^+ - a$ | $M^+ - (a+b)$ | b   |
|-------|-----------|---------------|-----|
| PND-0 | 489       | 471           | 18* |
| PND-1 | 531       | 471           | 60  |
| PND-2 | 545       | 471           | 74  |
| PND-3 | 559       | 471           | 88  |
| PND-4 | 573       | 471           | 102 |

*b = H₂O

It is presumed that the residues in 3-position are H for PND-0, acetyl for PND-1, propionyl for PND-2, isobutyryl for PND-3 and isovaleryl for PND-4. Also, comparison of PND-3 with the corresponding C-15003 P-3 reveals that P-3 gives $M^+ - a$ 573 and $M^+ - (a+b)$ 485 which are respectively lower by 14 mass units, thus suggesting that PND-3 is a compound corresponding to P-3 in which one methyl group in its nuclear structure has been replaced by a hydrogen atom. Moreover, comparison of the nuclear magnetic resonance spectra of the two compounds indicates methyl signals at δ3.18, 3.38 and 4.00 for P-3 while the signal at δ3.18 is absent in the case of PND-3. This means that the latter is a compound such that the N-CH₃ group on $C_{18}$ has been transformed into a NH group.

The same applies to PND-4, PND-2, PND-1 and PND-0, too. Based on the above data, PND-0, PND-1, PND-2, PND-3 and PND-4 are assumed to have the structures shown in FIG. 1.

FIG. 1

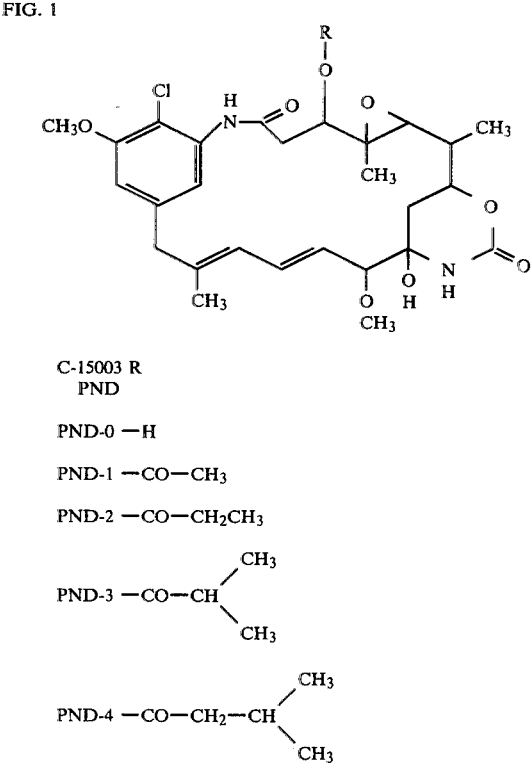

C-15003 R
PND

PND-0 —H

PND-1 —CO—CH₃

PND-2 —CO—CH₂CH₃

PND-3 —CO—CH(CH₃)₂

PND-4 —CO—CH₂—CH(CH₃)₂

(A) Antimicrobial activity

Using trypticase-soy-agar (Baltimore Biologicals, U.S.A.) as a test medium, the minimal inhibitory concentration of each compound against the following microorganisms was determined by the paper disk method. Thus, on plate media containing the following organisms, growth inhibition was investigated using paper disks (Toyo Roshi Corp., Japan thin-type, diam. 8 mm) imbibed with 0.02 ml of a 300 μg/ml solution of PND-1, PND-2, PND-3 or PND-4. The study showed that these compounds did not exhibit activity against the following microorganisms.

*Escherichia coli, Proteus vulgaris, Proteus mirabilis, Pseudomonas aeruginosa, Staphylococcus aureus, Bacillus subtilis, Bacillus cereus, Klebsiella pneumoniae, Serratia marcescens, Mycobacterium avium.*

On the other hand, on a plate assay medium [disodium phosphate 3.5 g, monopotassium phosphate 0.5 g, yeast extract (Difco, U.S.A.) 5 g, glucose 10 g, agar 15 g, distilled water 1000 ml, pH 7.0], a microbiological assay was carried out by the paper disk method using *Hamigera avellanea* IFO 7721 as a test organism. On said plate medium inoculated with said organism, growth inhibition was examined using a paper disk (Toyo Roshi Corp., Japan, Thin type, diam.8 mm) imbibed with 0.02 ml of a 100 μg/ml solution of PND-1, PND-2, PND-3 or PND-4. The diameters of zones of inhibition were 28 mm for PND-1, 30 mm for PND-2, 34 mm for PND-3 and 36 mm for PND-4.

On the other hand, *Tetrahymena pyriformis* W strain, as a test organism, was cultivated on an assay medium [Proteose-peptone (Difco) 20 g, yeast extract 1 g, glucose 2 g, distilled water 1000 ml, 1 M phosphate buffer (pH 7.0) 10 ml] at 28° C. for 44 to 48 hours and the minimal inhibitory concentrations of the antibiotics against said organisms were determined by the serial broth dilution method. It was thus found that PND-1 inhibits growth of the above organism at the concentration of 8 μg/ml, PND-2 at the concentration of 4 μg/ml, PND-3 at 2 μg/ml and PND-4 at 1 μg/ml.

(B) Antitumor activity

The therapeutic action of PND-1, PND-2, PND-3 and PND-4 against P388 tumor cell ($1 \times 10^6$ cell/mouse, intraperitoneal) was investigated. The results indicate that these compounds prolong the life span of a tumor-bearing mouse.

(C) Toxicity

In an acute toxicity test performed in mice, PND-1, PND-2, PND-3 and PND-4 were given to animals by the intraperitoneal route. The $LD_{100}$ and $LD_0$ of all these compounds were invariably 2.5 mg/kg and 0.313 mg/kg, respectively.

As described hereinbefore, PND have strong inhibitory actions against fungi and protozoa and are therefore valuable as antifungal or/and antiprotozoal agents. Moreover, PND are also considered to be useful as an antitumor agent in view of their action to increase the survival time of a tumor-bearing mammal (e.g. mouse).

PND can be used as antifungal or antiprotozoal agents in the following manner. Thus, the compounds can be advantageously used as a testing agent for the assay of bacterial ecology in a soil, activated sludge, animal fluid or other sample. Thus, for the purpose of separating useful bacteria from soil samples or for testing the actions of bacteria to the exclusion of protozoas in the operation and analysis of an active sludge system used in the treatment of waste water, the above compounds can be utilized to permit selective growth of bacterial life without allowing concomitant protozoa in the specimen to grow. An exemplary specific procedure comprises adding the specimen to a liquid or solid medium, then adding 0.1 ml of a 1% aqueous solution of methanol containing 10 to 100 μg/ml of this compound to each ml of the medium and incubating the mixture.

Because PND prolongs the survival times of warm-blooded animals (e.g. mouse, rat, dog, cat, etc.), these compounds can be used as antitumor drugs.

As an antitumor drug, PND can be administered orally or otherwise. Among routes other than oral, injection is preferred. Thus, PND may be administered subcutaneously, intraperitoneally, intravenously or intramuscularly, for instance. The dosage may range from about 5 to 800 μg/kg body weight/one dose, for instance, and be varied with reference to condition, animal species, etc. Such an injection can be prepared in the conventional manner. Thus, for example, about 50 μg to 3000 μg of the compound (I) of this invention is dissolved in about 0.5 ml of alcohol (e.g. methanol, ethanol), followed by addition of physiological saline to make a total of 10 ml. When the dose is small, the solution can be diluted with physiological saline.

PND-0 can be useful as a synthetic intermediate for the production of useful drugs.

For example, the compound of general formula (I) wherein R is a substituent group other than hydrogen can be produced by reacting PND-0 with the corresponding carboxylic anhydride in the presence of a base. The base may for example be a tertiary amine such as triethylamine, pyridine, 4-dimethylaminopyridine or the like. By the above method, any particular compound (I) wherein R is a substituent other than H (e.g. PND-2) can be produced.

The following Reference Examples and Examples are further illustrative of this invention.

REFERENCE EXAMPLE 1

In 1.0 ml of dichloromethane was dissolved 23.5 mg of P-0 and at about 22° C., 70.5 mg (about 10 mol equivalents) of acetic-formic anhydride (prepared by cooling 2 ml of acetic anhydride to −5° C. to 0° C., adding 1 ml of 99% formic acid thereto under stirring at −5° to 0° C. over a period of about 10 minutes, heating the mixture at 50° C. for 15 minutes and quenching it to 0° C.) and 11.7 mg of 4-dimethylaminopyridine. The mixture was stirred at room temperature (about 22° C.) overnight. Then, 10 drops of methanol were added to the reaction mixture and after stirring at room temperature for 3 hours, the reaction mixture was concentrated to dryness under reduced pressure. The residue was spotted on a silica gel preparative thin-layer chromatographic plate and developed twice with $H_2O$-saturated ethyl acetate. The silica gel at about 6.0 to 8.0 cm from the base line was scraped off and extracted with 10% methanoldichloromethane. The solvent was then distilled off under reduced pressure to obtain maytansinol formate [compound (II) where R=CHO] as a colorless glass-like substance.

REFERENCE EXAMPLE 2

The procedure of Reference Example 1 was applied to P-0 and valeric anhydride to obtain maytansinol 3-valerate [compound (II) where R=—$COCH_2CH_2CH_2CH_3$], m.p. 165°–168° C.

EXAMPLE 1

*Streptomyces minutiscleroticus* IFO 13361 was inoculated into a medium (pH 7.2) containing 1% dextrin, 1% glucose, 1% glycerol, 0.5% peptone, 0.5% yeast extract, 0.5% meat extract, 0.3% sodium chloride and 0.5% precipitated calcium carbonate, and cultivation was carried out under shaking at 28° C. for 22 hours. To 5 l of the resulting culture was added 1 g of P-3 and the reaction was carried out under shaking for 72 hours to obtain a reaction mixture. Thin-layer chromatography (TLC) of this reaction mixture showed that P-3 had decreased in amount and, instead, PND-3 had been produced.

EXAMPLE 2

To 5 l of the reaction mixture obtained in Example 1 was added 2.5 l of ethyl acetate, and extraction was carried out under stirring. The extract was suction-filtered through a Buchner's funnel precoated with 60 g of Hyflo Super Cel (Johnes Manville Sales Corp. U.S.A.). The above procedure was repeated twice. The ethyl acetate layers were combined and washed with 1.5 l of 1/200 N hydrochloric acid, twice with one liter of 1/10 M aqueous sodium carbonate and twice with one liter of water. The solution was dried over 30 g of anhydrous sodium sulfate and concentrated to 5 ml under reduced pressure followed by addition of 50 ml of petroleum ether, whereupon 1.04 g of crude product (i) was obtained. In a small amount of chloroform was dissolved 1 g of this crude product (i) and the solution was applied to the top of a column containing 100 ml of silica gel (Merck, Germany, 0.063–0.2 mm). Then, 200 ml of chloroform, 200 ml of chloroform-methanol (50:1) and 200 ml of chloroform-methanol (20:1) were passed through the column and the eluate was collected in 10 ml fractions. Each fraction was spotted on a silica gel glass plate (Kieselgel 60F$_{254}$, 0.25 mm, 20×20 cm) at 2.5 cm from the bottom edge and developed with chloroform-methanol (9:1) over a distance of about 17 cm. The fractions absorbing in ultraviolet light (2537 Å), i.e. fractions nos. 46 through 53 in the neighborhood of $R_f$ 0.49, are collected and concentrated under reduced pressure to a volume of about 2 ml. To the concentrate was added 50 ml of petroleum ether, whereupon 430 mg of a crude product (ii) was obtained. To 400 mg of the above crude product (ii) was added 15 ml of chloroform and after the solution was stirred with 2 g of silica gel (Kieselgel 60 F$_{254}$, 0.25 mm, 20×20 cm), the chloroform was distilled off under reduced pressure. The residue was applied to the top of a silica gel column (100 ml) and elution was carried out with 300 ml of n-hexane-ethyl acetate (1:3), 200 ml of the same (1:4) and 200 ml of ethyl acetate, the eluate being collected in 20 ml fractions. Each fraction was spotted on a silica gel glass plate (Kieselgel 60 F254 0.25 mm, 20×20 mm) and, after development with H$_2$O-saturated ethyl acetate, detection was carried out with ultraviolet light. The fractions absorbing in the neighborhood of $R_f$ 0.48, i.e. fractions nos. 27 through 33, were combined, concentrated and allowed to stand, whereupon PND-3 crystals were obtained (324 mg).

EXAMPLE 3

One gram of P-4 was added to 5 l of a culture broth of *Streptomyces minutiscleroticus* IFO 13361 as obtained in accordance with Example 1 and the reaction was carried out under shaking at 28° C. for 72 hours to obtain a reaction mixture. TLC assay of this reaction mixture showed that PND-4 had been produced therein.

EXAMPLE 4

The reaction mixture obtained in Example 3 was subjected to purification as Example 2 and subjected to TLC with the same developing solvent H$_2$O-saturated ethyl acetate as used in Example 2. The fractions around $R_f$ 0.55 were collected to recover a white powder of PND-4 (28 mg).

EXAMPLE 5

One gram of P-0 was added to 5 l of a culture broth of *Streptomyces minutiscleroticus* IFO 13361 as obtained in accordance with Example 1 and the reaction was carried out under shaking at 28° C. for 72 hours to obtain a reaction mixture. TLC assay of this reaction mixture showed that the amount of P-0 had decreased and, instead, PND-0 formed in the mixture.

EXAMPLE 6

One gram of P-1 was added to 5 l of a culture broth of *Streptomyces minutiscleroticus* IFO 13361 as obtained in accordance with Example 1 and the reaction was carried out under shaking at 28° C. for 72 hours to obtain a reaction mixture. TLC assay of this reaction mixture showed that the amount of P-1 had decreased and, instead, PND-1 formed in the mixture.

EXAMPLE 7

The reaction mixture obtained in Example 6 was subjected to purification as Example 2 and subjected to TLC with the same developing solvent H$_2$O-saturated ethyl acetate as used in Example 2. The fractions around $R_f$ 0.37 were collected to recover crystals PND-1 (34 mg).

EXAMPLE 8

One gram of P-2 were added to 5 l of a culture broth of *Streptomyces minutiscleroticus* IFO 13361 as obtained in accordance with Example 1 and the reaction was carried out under shaking at 28° C. for 72 hours to obtain a reaction mixture. TLC assay of this reaction mixture showed that the amount of P-2 had decreased and, instead, PND-2 formed in the mixture.

EXAMPLE 9

The reaction mixture obtained in Example 8 was subjected to purification as Example 2 and subjected to TLC with the same developing solvent H$_2$O-saturated ethyl acetate as used in Example 2. The fractions around $R_f$ 0.42 were collected to recover PND-2 crystals (26 mg).

EXAMPLE 10

One gram of P-3 was added to 5 l of a culture broth of *Streptomyces roseiscleroticus* IFO 13363 as obtained by cultivation in the same manner as Example 1 and the reaction was carried out under shaking at 28° C. for 72 hours to obtain a reaction mixture. TLC assay of this reaction mixture showed that the amount of P-3 had decreased and, instead, PND-3 formed in the mixture.

EXAMPLE 11

One gram of P-3 was added to 5 l of a culture broth of *Streptomyces flaviscleroticus* IFO 13357 as obtained by cultivation in the same manner as Example 1 and the reaction was carried out under shaking at 28° C. for 72 hours to obtain a reaction mixture. TLC assay of this reaction mixture showed that the amount of P-3 had decreased and, instead, PND-3 formed in the mixture.

EXAMPLE 12

One gram of P-0 was added to 5 l of a culture broth of *Streptomyces olivaceiscleroticus* IFO 13484 as obtained by cultivation in the same manner as Example 1 and the reaction was carried out under shaking at 28° C. for 72 hours to obtain a reaction mixture. TLC assay of this reaction mixture showed that the amount of P-0 had decreased and, instead, PND-0 formed in the mixture.

EXAMPLE 13

The reaction mixture obtained in Example 12 was purified in the same manner as Example 2 and subjected to TLC with the same developing solvent chloroform-methanol (9:1) used in Example 2. The fractions around $R_f$ 0.30 were collected to recover crystals of PND-0 (72 mg).

EXAMPLE 14

One milligram of P-0 was added to 5 ml of a culture broth of *Streptomyces sclerotialus* IFO 12246 as obtained by cultivation in the same manner as Example 1 and the reaction was carried out under shaking at 28° C. for 72 hours to obtain a reaction mixture. TLC assay of this reaction mixture showed that PND-0 had been produced therein.

EXAMPLE 15

One gram of P-0 is added to 5 l of a culture broth of *Chainia nigra* IFO 13362 as obtained by cultivation in the same manner as Example 1 and the reaction was carried out under shaking at 28° C. for 72 hours to obtain a reaction mixture. TLC assay of this reaction mixture showed that the amount of P-0 had decreased and, instead, PND-0 formed in the mixture.

EXAMPLE 16

In 8 ml of tetrahydrofuran was dissolved 200 mg of the crystalline PND-3 obtained in Example 2 and the solution was cooled to −5° C. To this solution was added 200 mg of lithium aluminum hydride. The reaction mixture was placed in an ice bath and stirred for 30 minutes. After addition of 10 ml of ethyl acetate, 10 ml of 1/200 N-HCl and 30 ml of a saturated aqueous solution of sodium chloride, extraction was performed with 200 ml of ethyl acetate. The ethyl acetate layer was washed with water, dried by the addition of anhydrous sodium sulfate and concentrated to dryness under reduced pressure. The residue was dissolved by the addition of a small amount of chloroform and applied to the top of a silica gel column (50 ml) and elution was carried out with 50 ml of chloroform, 200 ml of chloroform-methanol (25:1) and 100 ml of chloroform-methanol (9:1), the eluate being collected in 10 ml fractions. Each fraction was spotted on a silica gel glass plate and after development with H$_2$O-saturated ethyl acetate, the fractions, nos. 23 through 27, absorbing in the neighborhood of R$_f$0.25 were collected and concentrated to dryness. The residue was dissolved in a small amount of ethyl acetate and allowed to stand. The procedure provided crystals of PND-0 (77 mg). The physicochemical properties of this product were identical with those of the PND-0 obtained in Example 13.

EXAMPLE 17

50 mg of PND-3 was added to 1 l of a culture broth of *Streptomyces coelicolor* ATCC 13405 (IFO 3807) as obtained by cultivation in the same manner as Example 1 and the reaction was carried out under shaking at 28° C. for 2 days to obtain a reaction mixture. TLC assay of this reaction mixture showed that the amount of PND-3 had disappeared and, instead, PND-0 formed in the mixture.

EXAMPLE 18

The reaction mixture obtained in Example 17 was extracted with an equal volume of ethyl acetate and the extract was washed with water, dried over anhydrous sodium sulfate and concentrated under reduced pressure to recover 73 mg of residue. This residue was dissolved in 0.5 ml of chloroform and the solution subjected to preparative thin-layer chromatography using 12 silica gel glass plates (Kieselgel 60 F254). After development with H$_2$O-saturated ethyl acetate, the silica gel absorbing in the neighborhood of R$_f$0.25 is scraped off and extracted with ethyl acetate containing a small amount of water. The extract was washed with water, dried, concentrated under reduced pressure and allowed to stand. The above procedure provided crystals of PND-0 (24 mg). The physicochemical properties of these crystals were in agreement with those of PND-0 samples obtained in Examples 13 or 16.

REFERENCE EXAMPLE 3

In 0.5 ml of pyridine was dissolved 30 mg of PND-0, followed by addition of 0.2 ml of propionic anhydride. The mixture was stirred at room temperature (about 22° C.) overnight. Thereafter, the reaction mixture was worked up in the same manner as Reference Example 1. The above procedure provided 8 mg of PND-2.

What we claim is:

1. A compound of the formula:

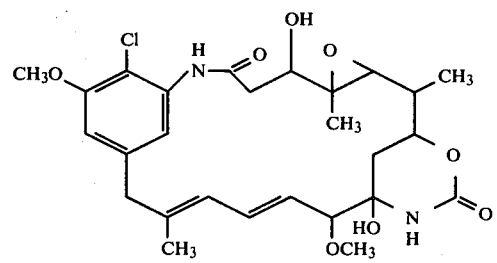

* * * * *